United States Patent [19]
Kelman

[11] Patent Number: 5,123,905
[45] Date of Patent: Jun. 23, 1992

[54] INTRAOCULAR LENS INJECTOR

[76] Inventor: Charles D. Kelman, 721 Fifth Ave., New York, N.Y. 10022

[21] Appl. No.: 712,357

[22] Filed: Jun. 7, 1991

[51] Int. Cl.$^5$ .............................................. A61B 17/00
[52] U.S. Cl. .................................. 606/107; 606/108; 604/15
[58] Field of Search ................. 606/107, 108; 623/6; 604/15, 16, 17, 18, 311, 232, 233

[56] References Cited

U.S. PATENT DOCUMENTS

| | | | |
|---|---|---|---|
| 668,879 | 2/1901 | Miller | 606/108 X |
| 940,519 | 11/1909 | Eastman | 604/15 |
| 2,351,836 | 6/1944 | Popper | 604/16 |
| 2,416,642 | 2/1947 | Popper | 604/15 |
| 3,421,509 | 1/1969 | Fiore | 606/108 X |
| 3,877,429 | 4/1975 | Rasumoff | 606/108 X |
| 4,033,349 | 7/1977 | Baehr | 606/107 |
| 4,211,234 | 7/1980 | Fisher | 606/108 X |
| 4,543,086 | 9/1985 | Johnson | 604/15 X |
| 4,716,901 | 1/1988 | Jackson et al. | 606/108 X |
| 4,836,201 | 6/1989 | Patton et al. | 606/107 |

Primary Examiner—Peter A. Aschenbrenner
Attorney, Agent, or Firm—Darby & Darby

[57] ABSTRACT

An injector head forming a hollow cone of spreadable leaves is partially inserted into a minimum size eye incision to inject a temporarily folded intraocular lens into the eye without stressing the incision. An injector device having a holder with a bore holding the lens in folded state is connected to the cone, and a plunger of the device inserted in the bore pushes the lens into and through the cone for controlled gradual injection into the eye and simultaneous controlled gradual unfolding therein.

15 Claims, 3 Drawing Sheets

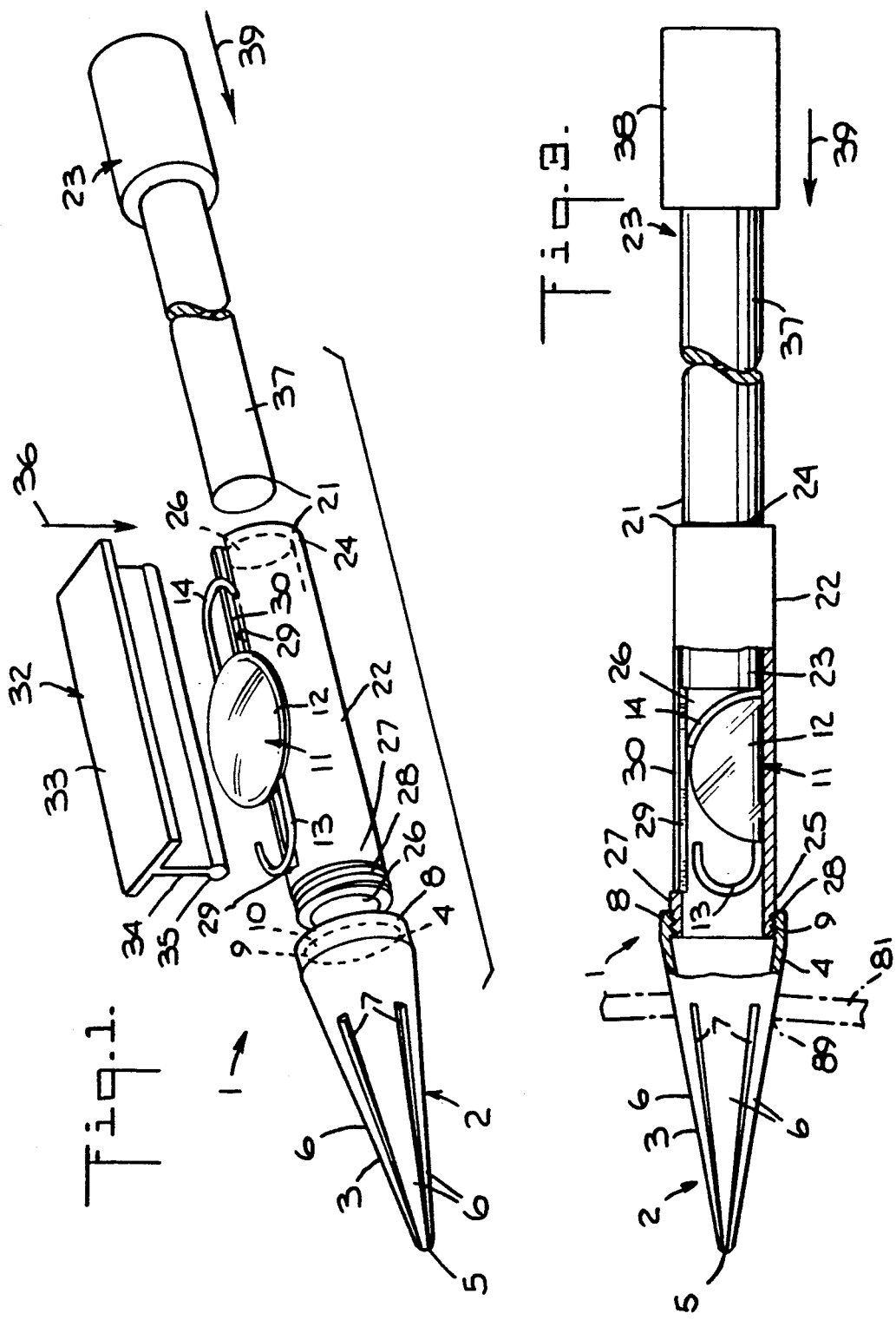

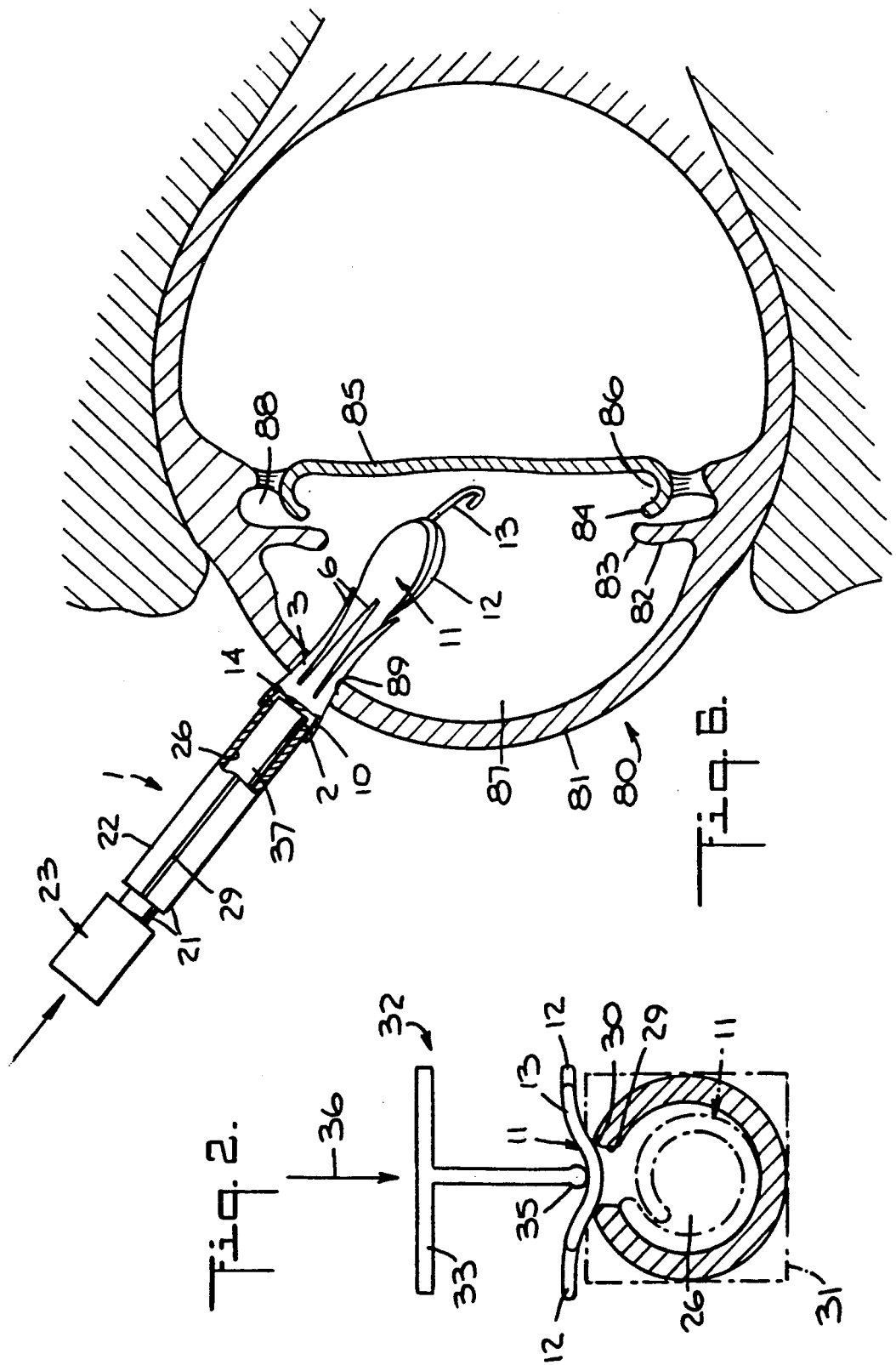

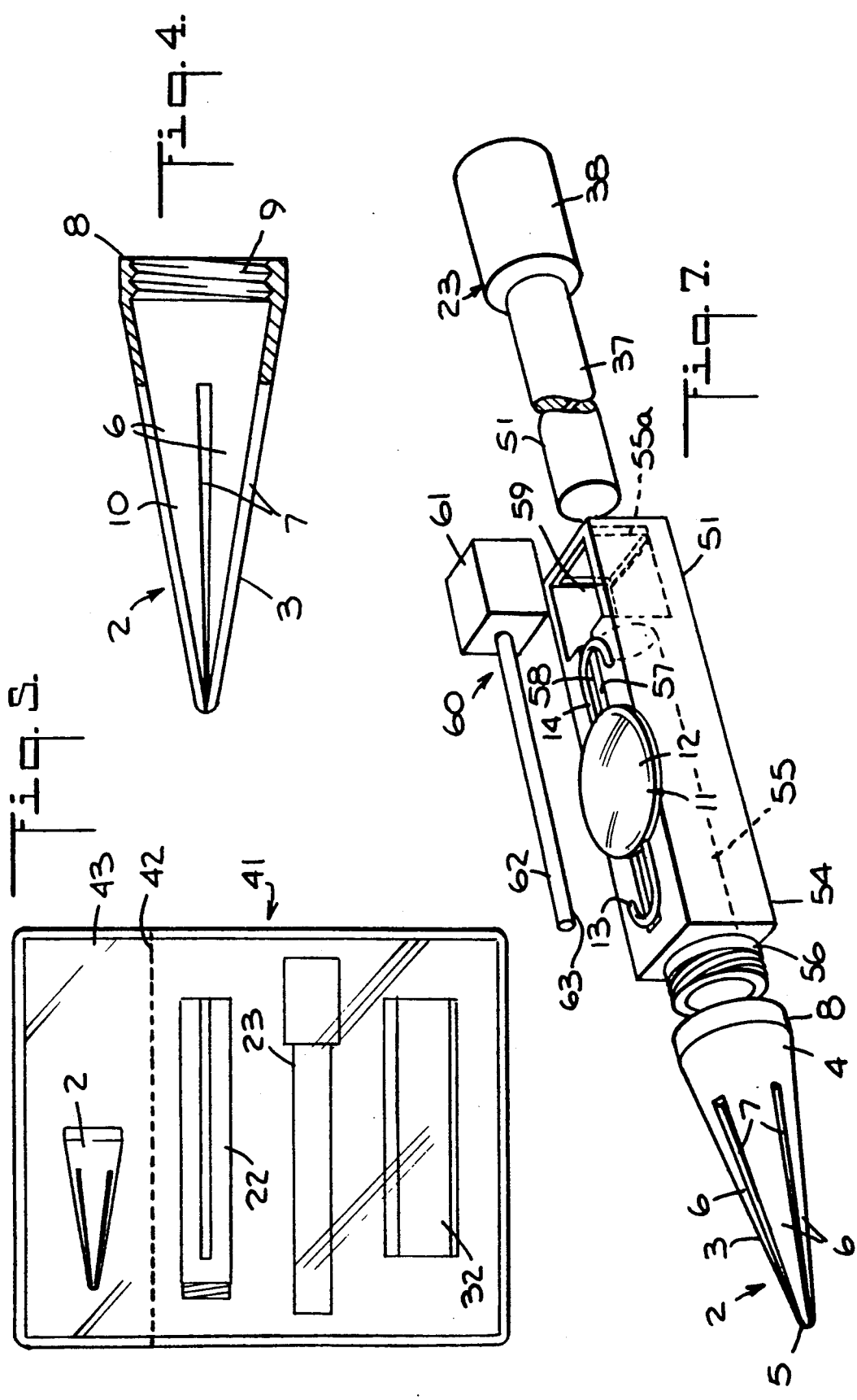

INTRAOCULAR LENS INJECTOR

FIELD AND BACKGROUND OF THE INVENTION

The present invention relates to an intraocular lens injector, and more particularly to an injector head forming a hollow cone of spreadable leaves for partial insertion into a minimum size eye incision to inject a temporarily folded, i.e. deformable, intraocular lens into the eye, and to an assembly of the cone and an injector device having a holder with a bore to hold the folded lens and connected to the cone, and a plunger to push the lens from the bore and through the cone for controlled gradual injection into, and simultaneous controlled gradual unfolding within, the eye, and a method of so using the assembly.

In eye surgery for treating conditions such as natural eye lens cataracts, a common procedure is to remove the cataracted lens through an incision in the cornea of the eyeball, and replace it by an artificial intraocular lens. The intraocular lens, typically 6 mm in diameter, is usually temporarily resiliently deformable, i.e. foldable into generally cylindrical shape, by curling, etc., to reduce its girth, and while kept folded is inserted through a corneal incision, typically 3.5-4 mm long, to minimize patient trauma. The lens has a lens body or optic, e.g. of soft material such as silicone, with normally stiffer resiliently deformable position fixation means or haptics, e.g. of polypropylene, extending therefrom to seat the lens in the eye.

The haptics are kept in stable relation to the folded lens body during insertion into the eye so as to pass without difficulty through the incision. Once inserted, unfolding the lens body and haptics in the confined space at the implantation site must be controlled to avoid patient trauma from contact of these expanding mechanical elements with the inner wall of the cornea or other eye parts. Inserting the folded lens into an eye so as to minimize patient trauma is very difficult. A tool is needed to hold and insert the folded lens, requiring an incision large enough to accommodate both. Often, a separate retainer keeps the lens folded, so that the inserted retainer and tool clutter the eye interior during lens unfolding, after which the tool and retainer must be retrieved via the incision.

U.S. Pat. No. 4,573,998 to Mazzocco shows various tools to insert a deformable lens through an incision into the eye by pushing, stretching, ejecting or compressing technique. The lens and/or tool grossly contact the incision during insertion and the lens must be released carefully in the eye to keep the expanding lens elements from injuring internal eye parts.

U.S. Pat. No. 4,906,247 to Fritch shows a deformable lens held folded by forceps inserted in a stretchable plastic tube so as to stretch the tube diameter and also squeeze the tube around the folded lens like a mitten. Upon inserting the lens into the eye, the forceps must release it with great care to keep the expanding lens elements from injuring internal eye parts.

U.S. Pat. No. 4,911,714 to Poley shows a deformable lens held folded by sutures connecting apertures on opposed edges of the lens, or by integral lock means or adhesive on such edges, for insertion by a first tool through a first incision into the eye. A second tool inserted through a second incision is used to cut and remove the sutures, unlock the lock means or break the adhesive bond while the first tool holds the lens to keep the expanding lens elements from injuring internal eye parts.

U.S. Pat. No. 4,917,680 to Poley shows a deformable lens held folded by a severable retainer or band for insertion by a first tool through a first incision into the eye. A second tool inserted through a second incision is used to sever and remove the band while the first tool holds the lens to keep the expanding lens elements from injuring internal eye parts.

U.S. Pat. No. 4,976,716 to Cumming shows an insertion device with telescoping inner and outer tubes, and a plunger in the inner tube, for a deformable lens having leading and trailing haptics. Two opposed flexible, widely diverging, inner fingers integral with the inner tube front are notched near their free ends to form bendable tips. Two opposed rigid outer fingers pivoted to the outer tube front are lockable to hold the inner fingers in narrower diverging state when the inner tube is retracted in the outer tube so that only its tips protrude. Jaws on a lens loading tray squeeze and fold the lens between the inner fingers so that the leading haptic protrudes from their narrower diverging tips, and then the outer fingers are locked.

The leading haptic and diverging finger tips are inserted into the eye incision, and a lever and ratchet drive on the device is used to move the inner tube and plunger forwardly of the outer tube until the inner finger notches clear the incision, enabling the stored force of the folded lens to bend the inner finger tips outwardly of their widely diverging position for partial lens unfolding. Further use of the drive causes the plunger to push the lens beyond the inner finger tips for complete lens unfolding. A spring return of the drive is used to retract the plunger and inner tube from the incision. The device is complex, costly and cumbersome to operate, and its diverging fingers stress the incision or require use of a larger incision. As the fingers do not surround the folded lens, but only hold its diametrically opposed girth portions, the outwardly projecting girth portions therebetween can contact and stress the incision and inner wall of the cornea during the insertion procedure.

Also, a device manufactured by Allergen Inc., known as "The Prodigy," includes a lens injector having a straight, rigid tubular portion whose tip is inserted into the incision and through which the folded lens is injected into the eye. The tip is not tapered and has no means to control unfolding of the lens.

It would be desirable to insert a temporarily folded intraocular lens through a minimum size incision into the eye by an instrument that does not unduly stress or traumatize the incision, permitting controlled gradual lens injection and unfolding in the confined space within the eye, while avoiding incision trauma from such stress or contact of the unfolding lens with the inner wall of the cornea or other eye parts.

SUMMARY OF THE INVENTION

It is an object of the invention to overcome prior art drawbacks, and to provide an intraocular lens injector having a head for partial insertion into a minimum size eye incision to inject a temporarily folded, i.e. deformable, intraocular lens into the eye, and a device to push the folded lens through the head, and a method of using the injector for controlled gradual injection of the lens into the eye and simultaneous controlled gradual unfolding thereof within the eye, so as to avoid patient trauma from stress on the incision or contact of the unfolding lens with the inner wall of the cornea or other eye parts.

It is another object of the invention to provide such an injector of structurally simple parts, readily fabricated at relatively low cost so as to be economically feasible for it to be disposable.

According to the invention, an injector head is provided for partial insertion into a minimum size eye incision to inject a temporarily folded intraocular lens into the eye. The head comprises a hollow cone having a base end and a generally pointed end, and defines a plurality of circumferentially distributed cantilever leaves convergingly tapering from the base end to the generally pointed end. The leaves are resiliently flexible for outward displacement from a normally closed position in which they are adjacent each other to an open position in which they are spread apart to allow the folded lens to be injected through the cone into the eye.

The base end has a mounting formation adapted to mount the head on an injector device adapted for controlled gradual injection of the folded lens through the cone and into the eye. The leaves in closed position are in generally side by side abutting contact, and are sufficiently flexible for displacement to open position under the urging contact force of the folded lens being injected through the cone. The head may be provided in sterile packaged form.

The invention also concerns an injector assembly comprising the injector head and the injector device. The device comprises a holder and a plunger. The holder has a plunger end and a delivery end interconnected by a longitudinal through bore adapted to hold the folded lens, and a longitudinal slot generally parallel to the bore and communicating the bore with the exterior of the holder. The delivery end is connected to the base end of the cone for connecting the bore with the cone. The plunger is insertable into the bore from the plunger end for controlled gradual delivery of the lens from the delivery end into and through the cone for controlled gradual injection of the lens into the eye and simultaneous controlled gradual unfolding of the lens within the eye.

The holder slot preferably has a V-shaped entrance. Typically, a lens inserter is included having a longitudinal contact edge for forcing the lens in unfolded state at the exterior of the holder, against and inwardly through the slot into the bore, to provide the lens in folded state in the bore. The inserter may include a plate portion having a bulbous longitudinal contact edge, or a pin portion defining a round longitudinal contact edge. The assembly may be provided as a kit containing the head, holder and plunger, and optionally the inserter, in sterile packaged form.

According to the invention, a method of using the assembly is also provided to inject the intraocular lens into the eye.

The method comprises placing a lens atop the longitudinal slot, forcing the lens through the slot by applying a longitudinal edge, e.g. of the inserter, thereto for folding the lens in the holder bore, moving the plunger into the bore from the plunger end, partially inserting the cone into a minimum size eye incision, and gradually pushing the plunger against the lens in the bore to deliver it into the cone and urge it against the leaves to spread them apart without unduly stressing the incision, for controlled gradual lens injection into the eye and simultaneous controlled gradual lens unfolding within the eye preparatory to implanting the lens therein.

Generally, the lens has a pair of opposed haptics, and is provided in the bore with one haptic ahead of the lens as a leading haptic and the other behind the lens as a trailing haptic, so that the leading haptic is injected into the eye ahead of the lens for movement away from the incision as the lens enters and unfolds in the eye, followed by insertion of the trailing haptic.

BRIEF DESCRIPTION OF THE DRAWINGS

Other objects of the invention will become apparent from the within specification and accompanying drawings, in which:

FIG. 1 is a perspective view of an assembly of an injector head and an injector device therefor, together with a lens inserter to insert the lens in the device, according to a first embodiment of the invention;

FIG. 2 is a cross sectional view showing the loading of the lens into the device via the inserter;

FIG. 3 is a side view, partially sectioned and broken away, of the head and device, assembled for use with the lens loaded therein in folded state;

FIG. 4 is a longitudinal sectional view of the head;

FIG. 5 is a view of the head, device and inserter as a combined assembly in a sterile package;

FIG. 6 is a schematic view showing the lens as it unfolds during injection via the head and device into the eye; and FIG. 7 is a schematic view of an assembly of the head with an injector device and a lens inserter according to a second embodiment of the invention.

DESCRIPTION OF THE PREFERRED EMBODIMENTS

Referring to the drawings, and initially to FIGS. 1-6, an assembly 1 is shown of an injector head 2 for partial insertion into a minimum size eye incision to inject a temporarily folded intraocular lens 11 into the eye, and an injector device 21 for use with head 2, plus a lens inserter 32 for inserting lens 11 into device 21, according to a first embodiment of the invention.

Lens 11 is conventional, having a temporarily foldable, i.e. resiliently deformable, optic or lens body 12 and a pair of opposed resiliently deformable position fixation means or haptics for seating the lens in the eye, including a leading haptic 13 and a trailing haptic 14. Lens 11 is capable of being temporarily folded under compression force into a compact, e.g. cylindrical, shape of reduced girth for facilitated insertion through a minimum size incision into the eye, and of unfolding to original undeformed state upon release of such compression force.

Head 2 is formed of a hollow split cone 3 with a fixed base end 4 and a generally pointed, openable tip end 5. Cone 3 defines a plurality of, e.g. four, circumferentially distributed, cantilever leaves 6 convergingly tapering from base end 4 to tip end 5, formed by slits 7. Leaves 6 are resiliently flexible for outward displacement from a normally closed position adjacent each other (FIGS. 3 and 4), e.g. in side by side abutting contact, to an open position in which they are spread apart to allow lens 11 to be injected through cone 3 into the eye (FIG. 6). Leaves 6 are sufficiently flexible for displacement to open position under the urging contact force of lens 11 as it is being injected through cone 3.

Device 21 includes a holder 22 and a plunger 23. Holder 22 has a plunger end 24 and a delivery end 25 interconnected by a longitudinal through bore 26 to hold folded lens 11.

Base end 4 has a mounting formation, e.g. a collar 8 with internal threads 9 in the interior 10 of cone 3. Delivery end 25 has a counterpart mounting formation engageable with such mounting formation, e.g. a neck 27 with external threads 28 mating with threads 9 on collar 8 (FIG. 3), to mount head 2 on device 21 and connect bore 26 with interior 10. The mounting formation and counterpart formation may be of any other suitable form, such as a rib on one of these parts and a groove on the other, sized for snap fit releasable interlocking to mount cone 3 on holder 22 and communicate interior 10 with bore 26. Also, base end 4 may be integrally connected to delivery end 25.

Plunger 23 is inserted in bore 26 via plunger end 24 for controlled gradual delivery of lens 11 from delivery end 25 into and through interior 10 for controlled gradual injection into the eye and simultaneous controlled gradual unfolding therein. Bore 26 may be of circular or other suitable, e.g. oval or polygonal, cross sectional shape for holding and delivering lens 11 in folded state, with plunger 23 being of conforming shape.

To load lens 11, holder 22 has a longitudinal slot 29 generally parallel to bore 26 and which communicates bore 26 with the exterior of holder 22. Slot 29 may extend from just behind delivery end 25 to the extreme edge of plunger end 24.

As shown in FIG. 1, a lens inserter 32, e.g. formed as a T-shaped member by a horizontal press block 33 and a vertical plate 34 attached to its underside, is included to force lens 11 in unfolded state at the exterior of holder 22, against and inwardly through slot 29 into bore 26 to load lens 11 in folded state therein. Lens 11 is protected from damage during such loading by providing slot 29 with a V-shaped entrance 30 (FIG. 2), and the bottom of plate 34 with a bulbous longitudinal contact edge 35. Plate 34 and edge 35 are desirably coextensive with slot 29.

Lens 11 may be loaded into holder 22 by pressing inserter 32 with one hand in the direction of arrow 36 against unfolded lens 11 resting across slot 29, while palming holder 22 in the other hand. By providing holder 22 with a polygonal external profile, e.g. a rectangular block shape 31 as shown in phantom in FIG. 2, holder 22 may be placed on a table or other support and lens 11 loaded by pressing inserter 32 with only one hand to fold lens 11 into bore 26 via slot 29. Slot 29 is sized to receive the composite thickness of contact edge 35, plate 34 and the folded thickness of lens 11, for inserting lens 11 into bore 26 without hindrance or damage.

Once lens 11 is loaded in holder 22 and inserter 32 is removed, the plunger shank 37 is inserted in bore 26 via plunger end 24 and pushed by the plunger handle 38 in the direction of arrow 39 until plunger 23 forces trailing haptic 14 forward and abuts lens body 12. Head 2 is then mounted on holder 22 to form assembly 1 (FIG. 3). Head 2 is partially inserted into the incision 89 in the cornea 81 (shown in phantom in FIG. 3). Plunger 23 is pushed in the direction of arrow 39 to force lens 11 from bore 26 into interior 10, and against surrounding leaves 6 to spread them apart for controlled gradual injecting of lens 11 into the eye and simultaneous controlled gradual unfolding as it exits from head 2 (FIG. 6).

Head 2 may be provided alone, or with the components of device 21, optionally including inserter 32, in kit form, in a sterile package 41, e.g. with a separation 42 providing head 2 in a sub-package 43 distinct from holder 22 and plunger 23, and optionally inserter 32 (FIG. 5).

As shown in FIG. 6, the pertinent parts of the human eyeball 80 include the cornea 81, the iris 82 with its central opening or pupil 83, the remainder of the anterior lens capsule 84 after extracapsular removal of a cataracted natural lens, and the posterior lens capsule 85, such that posterior capsule 85 defines a cul-de-sac 86 at its peripheral margins that is formed between anterior and posterior capsules 84, 85. The aqueous humor zone between cornea 81 and posterior capsule 85 is divided by iris 82 into an anterior chamber 87 and a posterior chamber 88.

Haptics 13, 14 may seat in cul-de-sac 86, between anterior and posterior capsules 84, 55, to position lens 11 so that lens body 12 performs its light focusing function.

Typically, lens body 12 has a diameter of about 5-6 mm and a thickness of about 0.4 mm, and haptics 13, 14 have a thickness of about 0.2 mm and a width of about 1.2 mm. Haptics 13, 14 may have a composite expanded length in undeformed state of about 13 mm from the outer edge of one haptic to the diametrically opposite outer edge of the other. As folded, lens body 12 typically has a girth diameter of about 3 mm, permitting its facile insertion through an eye incision at most about 3.5 mm long.

Since folded lens 11 is of bowed shape as loaded in bore 26 (shown in phantom in FIG. 2), the diameter of bore 26 may roughly equal the, e.g. about 3 mm, girth diameter of folded lens body 12, enabling lens 11 to be pushed by plunger 23 along bore 26 and into cone interior 10 easily and without hindrance or damage.

Lens body 12 may be of any suitable temporarily resiliently deformable light focusing optic serving material that is sufficiently soft for the desired folding and also non-toxic and eye fluid compatible such as silicone, with haptics 13, 14 typically being of slightly stiffer resiliently deformable material such as polypropylene. Lens body 12 must have a memory, so that when folded to reduce its girth, it will return readily to unfolded state, so long as promptly inserted through the incision for unfolding in the eye, thus insuring against loss of such memory. Of course, the lens folding and injection procedures are effected under sterile conditions.

Such folding must be done during or just prior to surgery to avoid the loss of "memory" of the lens which would take place if "folded" by the manufacturer days or weeks before surgery.

As used herein, "folding" means doubling, rolling, curling, gathering, crinkling, and like type compressing of lens body 12 onto itself one or more times to reduce its composite girth.

As shown in FIG. 6, to inject lens 11, a minimum size corneal incision 89 is made by the surgeon, e.g. about 3.5 mm long, just sufficient to accommodate the reduced girth of folded lens body 12. Then, holding assembly 1 with head 2 adjacent incision 89, cone 3 is inserted partially thereinto so as not to stress unduly incision 89, and plunger 23 is gradually pushed in bore 26 to force lens 11 into interior 10 and against surrounding leaves 6 to cause them to spread apart as lens 11 starts to unfold in the eye. As the leading end 100 of cone 3 is located inwardly of incision 89, the spreading of cantilever leaves 6 occurs without stressing incision 89.

Continued gradual pushing of plunger 23 results in injection of lens 11 into the eye and its gradual unfolding to normal state. During this unfolding, the free ends of leaves 6 readily distend outwardly beyond the normal confines of cone 3 without stressing incision 89 as leaves 6 inwardly clear incision 89. Trailing haptic 14 may remain outside incision 89 and assembly 1 simply removed to release cone 3 therefrom, whereupon forceps are used to "snake" haptic 14 through incision 89 and seat lens 11 in the eye in the usual way.

Assembly 1 thus injects lens 11 into the eye without inserting head 2 fully into incision 89. Forceps are only used to insert trailing haptic 14 fully and seat lens 11 in the eye after head 2 is removed from incision 89, thus avoiding stress on the incision. As lens 11 is controlled by the gradual movement of plunger 23, it is gradually injected and gradually unfolds in controlled manner by the surrounding leaves 6, thus preventing the lens from bursting open, in uncontrolled manner, from its closed state, and in turn avoiding contact of the entering and unfolding lens 11 with the inner wall of cornea 81 or other eye parts.

Heretofore, when a tool was used to insert a folded lens, it fully occupied the incision along with the lens, causing patient trauma by stressing the incision or by increasing its size.

In using assembly 1, preliminarily lens 11 is provided in folded state in bore 26, formation 8 is engaged with counterpart formation 27 to connect cone 3 to bore 26, and plunger 23 is inserted in bore 26 via plunger end 24. Then, cone 3 is partially inserted into incision 89 so as to avoid stressing it, and plunger 23 gradually pushed against lens 11 in bore 26 to deliver it to cone 3 and urge it against leaves 6 to spread them apart without stressing the incision, for controlled gradual injection of lens 11 into the eye and simultaneous controlled gradual unfolding of it therein.

Typically, leading haptic 13 is injected ahead of lens body 12 and moves away from incision 89 as lens 11 enters and unfolds in the eye, followed by trailing haptic 14 insertion and lens 11 implanting by seating haptics 13, 14 against adjacent eye tissue.

Assembly 1 facilitates exploitation of the minimum size incision used for extracapsular removal of the natural lens, as head 2 may be partially inserted in that same incision to inject lens 11 into the eye. This is significant as the smaller the incision size the less the patient trauma, including pain and discomfort then and later, not only due to the incision itself but also to the number and/or size of any needed sutures.

Referring to FIG. 7, a second embodiment of an assembly 50 is shown having the same head 2 and plunger 23 as in the embodiment of FIGS. 1-6, but a holder 52 of different type forming an injector device 51 with plunger 23. Holder 52 has a plunger end 53 and a delivery end 54 interconnected by a longitudinal through bore 55 to hold folded lens 11. Delivery end 54 has a counterpart mounting formation engageable with mounting formation 8, e.g. a neck 56 with external threads (not shown), mating with threads 9, to mount head 2 on device 51 and connect bore 55 with interior 10. Plunger 23 is inserted in bore 55 via plunger end 53 for delivery of lens 11 from delivery end 54 into and through interior 10, for use of device 50 in the same way as device 21.

To load lens 11, holder 52 has a longitudinal slot 57 generally parallel to bore 55 and which communicates bore 55 with the exterior of holder 52. Holder 52 is of rectangular external profile or shape and longer than holder 22 to accommodate a suitably shaped, e.g. rectangular, recess 59 at the rear end of slot 57 and communicating therewith. Slot 57 may extend from just behind delivery end 54 to recess 59. Recess 59 communicates with the rear face of plunger end 53 via a bore extension 55a.

A lens inserter 60, e.g. formed by a rear press block 61 and a horizontally extending front pin 62 attached thereto, is included to force unfolded lens 11 at the exterior of holder 52, against and inwardly through slot 57 into bore 55 to load lens 11 in folded state therein. Lens 11 is protected from damage during such loading by providing slot 57 with a V-shaped entrance 58 and pin 62 with a round cross section forming a longitudinal contact edge 63. Pin 62 is desirably coextensive with slot 57. Press block 61 is sized and shaped for play-free, sliding fit in recess 59 for downward movement therein to move pin 62 via slot 57 into bore 55. Bore extension 55a is sized to accommodate press block 61 for rearward removal of inserter 60 therethrough after lens 11 is loaded in bore 55.

Holder 52 has a rectangular external profile to facilitate loading of lens 11, by resting holder 52 on a table or other support, and using one hand to force press block 61 downwardly in a manner similar to the loading of holder 22. Slot 57 is sized to receive the composite thickness of pin 62 and the folded thickness of lens 11 to insert lens 11 into bore 55 without hindrance or damage. Lens 11 is loaded in holder 52 in folded or otherwise compacted, e.g. cylindrically rolled, state to reduce its composite girth, and is delivered without hindrance or damage in that state from holder bore 55 to interior 10 for insertion via head 2 through incision 89 into the eye.

Once lens 11 is loaded in holder 52, inserter 60 is pulled out rearwardly. Then, plunger shank 37 is inserted in bore 55 via plunger end 24 for the above described purposes, and head 2 is mounted on holder 52 to form assembly 50.

Head 2 may also be mounted on the tubular tip of a lens insertion instrument, like the aforesaid Allergen Inc. device known as "The Prodigy," suitably modified for connecting head 2 thereon, for use with plunger 23, to achieve the purposes of the present invention.

Head 2 may be of any suitable non-toxic material, e.g. rigid or resiliently flexible plastic, with at least leaves 6 being of resiliently flexible material, e.g. resiliently flexible plastic. Holders 22 and 52, plunger 23 and inserters 32 and 60, may be of suitable rigid material, e.g. metal or plastic such as Teflon. Head 2 may be a single use disposable part, and holders 22 and 52, plunger 23 and inserters 32 and 60 may be reusable parts.

Clearly, the injector head, injector device and lens inserter of the invention are structurally simple parts that are readily fabricated at relatively low cost.

The specification and drawings are set forth by way of illustration and not limitation, and various modifications may be made therein without departing from the spirit of the invention which is to be limited solely by the scope of the claims.

What is claimed is:

1. Injector head for partial insertion into a minimum size eye incision to inject a temporarily folded intraocular lens into the eye, comprising a hollow cone having a base end and a generally pointed end, and defining a plurality of circumferentially distributed, cantilever leaves convergingly tapering from the base end to the generally pointed end, the leaves being sufficiently resiliently flexible for outward displacement from a normally closed position in which they are adjacent each other to an open position in which they are spread apart outwardly beyond the normal confines of the cone under the urging contact force of such folded lens, upon being injected through the cone, so as to allow such folded lens to be injected from the cone into the eye.

2. Head of claim 1 wherein the base end has a mounting formation adapted to mount the head on an injector device adapted for controlled gradual injection of such folded lens through the cone and into the eye.

3. Head of claim 1 wherein the leaves in closed position are in generally side by side abutting contact.

4. Head of claim 1 wherein the head is in sterile packaged form.

5. Injector assembly comprising an injector head portion for partial insertion into a minimum size eye incision to inject a temporarily folded intraocular lens into the eye, and an injector device portion, the head portion comprising a hollow cone having a base end and a generally pointed end, and defining a plurality of circumferentially distributed, cantilever leaves convergingly tapering from the base end to the generally pointed end, the leaves being resiliently flexible for outward displacement from a normally closed position in which they are adjacent each other to an open position in which they are spread apart to allow such folded lens to be injected through the cone into the eye, and the device portion comprising a holder having a plunger end and a delivery end interconnected by a longitudinal through bore adapted to hold such folded lens, and a longitudinal slot generally parallel to the bore and communicating the bore with the exterior of the holder, the delivery end being connected to the base end of the cone for connecting the bore with the cone, and a plunger insertable into the bore from the plunger end for controlled gradual delivery of the lens from the delivery end into and through the cone for controlled gradual injection of the lens into the eye and simultaneous controlled gradual unfolding of the lens within the eye.

6. Injector assembly comprising an injector head portion for partial insertion into a minimum size eye incision to inject a temporarily folded intraocular lens into the eye, and an injector device portion, the head portion comprising a hollow cone having a base end and a generally pointed end, and defining a plurality of circumferentially distributed, cantilever leaves convergingly tapering from the base end to the generally pointed end, the leaves being resiliently flexible for outward displacement from a normally closed position in which they are adjacent each other to an open position in which they are spread apart to allow such folded lens to be injected through the cone into the eye, and the device portion comprising a holder having a plunger end and a delivery end interconnected by a longitudinal through bore adapted to hold such folded lens, and a longitudinal slot generally parallel to the bore and communicating the bore with the exterior of the holder, the delivery end being connected to the base end of the cone for connecting the bore with the cone, and a plunger insertable into the bore from the plunger end for controlled gradual delivery of the lens from the delivery end into and through the cone for controlled gradual injection of the lens into the eye and simultaneous controlled gradual unfolding of the lens within the eye;

wherein a lens inserter is included having a longitudinal contact edge for forcing the lens in unfolded state at the exterior of the holder, against and inwardly through the slot into the bore, to provide the lens in folded state in the bore.

7. Assembly of claim 6 wherein the slot has a V-shaped entrance.

8. Assembly of claim 6 wherein the inserter includes a plate portion having a bulbous longitudinal contact edge.

9. Assembly of claim 6 wherein the inserter includes a pin portion defining a round longitudinal contact edge.

10. Assembly of claim 5 in the form of a kit containing the head portion, holder and plunger in sterile packaged form.

11. Assembly of claim 6 in the form of a kit containing the head portion, holder, plunger and inserter in sterile packaged form.

12. Method of using the assembly of claim 5 to inject a temporarily folded intraocular lens into an eye, comprising placing such a lens in unfolded state across the longitudinal slot of the holder, forcing the lens through the slot by applying a longitudinal edge thereto for folding the lens in the holder bore, moving the plunger into the bore from the plunger end, partially inserting the cone into a minimum size eye incision, and gradually pushing the plunger against the folded lens in the bore to deliver the lens into the cone and urge it against the leaves to spread the leaves apart without unduly stressing the incision, for controlled gradual injection of the lens into the eye and simultaneous controlled gradual unfolding of the lens within the eye preparatory to implanting the lens therein.

13. Method of claim 12 wherein the lens has a pair of opposed haptics and the lens is provided in the bore with one haptic ahead of the lens as a leading haptic and the other haptic behind the lens as a trailing haptic, so that the leading haptic is injected into the eye ahead of the lens for movement away from the incision as the lens enters and unfolds in the eye, followed by insertion of the trailing haptic.

14. Method of using the assembly of claim 6 to inject a temporarily folded intraocular lens into an eye, comprising placing such a lens in unfolded state across the longitudinal slot of the holder, forcing the lens through the slot by applying the longitudinal edge of the inserter thereto for folding the lens in the holder bore, moving the plunger into the bore from the plunger end, partially inserting the cone into a minimum size eye incision, and gradually pushing the plunger against the folded lens in the bore to deliver the lens into the cone and urge it against the leaves to spread the leaves apart without unduly stressing the incision, for controlled gradual injection of the lens into the eye and simultaneous controlled gradual unfolding of the lens within the eye preparatory to implanting the lens therein.

15. Method of claim 14 wherein the lens has a pair of opposed haptics and the lens is provided in the bore with one haptic ahead of the lens as a leading haptic and the other haptic behind the lens as a trailing haptic, so that the leading haptic is injected into the eye ahead of the lens for movement away from the incision as the lens enters and unfolds in the eye, followed by insertion of the trailing haptic.

* * * * *